US008178293B2

(12) United States Patent
Bernard et al.

(10) Patent No.: US 8,178,293 B2
(45) Date of Patent: May 15, 2012

(54) USES OF BNIPXL-BETA IN PREMATURE CANITIES

(75) Inventors: Bruno Bernard, Courbevoie (FR); Stéphane Commo, Chaville (FR); Olivier De Lacharriere, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/387,138

(22) Filed: Apr. 28, 2009

(65) Prior Publication Data
US 2009/0275033 A1    Nov. 5, 2009

(30) Foreign Application Priority Data

Apr. 30, 2008    (FR) ...................................... 08 02435

(51) Int. Cl.
*C12Q 1/68* (2006.01)
*C12N 15/85* (2006.01)
(52) U.S. Cl. .......................................... 435/6; 435/325
(58) Field of Classification Search ........................ None
See application file for complete search history.

(56) References Cited

FOREIGN PATENT DOCUMENTS
WO    WO 2004/007742 A2    1/2004

OTHER PUBLICATIONS

European Search Report issued May 20, 2009 in connection with European Patent Application No. EP 09 15 9080.
French Search Report issued Nov. 6, 2008 in connection with French Patent Application No. 08/02435.
Belcredito S. et al., "Estrogen neuroprotection: the involvement of the Bcl-2 binding protein BNIP2," *Brain Research Reviews*, vol. 37, pp. 335-342, published 2001.
Blouin J.L. et al., "Localisation of a gene for Human Premature Hair Greying on chromosome 9q34," *Congress of the American Society of Human Genetics*, published Oct. 2006.
Commo S. et al., "Melanocyte Subpopulation Turnover During the Human Hair Cycle: An Immunohistochemical Study," *Pigment Cell Research*, vol. 13, pp. 253-259, published 2000.
Commo S. et al., "Absence of TRP-2 in Melanogenic Melanocytes of Human Hair," *Pigment Cell Research*, vol. 17, pp. 488-497, published 2004.
Commo S. et al., "Human hair greying is linked to a specific depletion of hair follicle melanocytes affecting both the bulb and the outer root sheath," *British Journal of Dermatology*, vol. 150, pp. 435-443, published 2004.
Formstecher E. et al., "Protein interaction mapping: A *Drosophila* case study," *Genome Research*, vol. 15, pp. 376-384, published 2005.
Fromont-Racine M. et al., "Toward a functional analysis of the yeast genome through exhaustive two-hybrid screens," *Nature Genetics*, vol. 16, pp. 277-282, published 1997.

de Lacharrière O. et al., "Genetics of Hair Greying: A Putative Gene for Premature Hair Greying Maps to Chromosome 9q34," *World Congress of Dermatology*, Oct. 2007.
Machida T. et al., "Increased expression of proapoptotic *BMCC1*, a novel gene with the BNIP2 and Cdc42GAP homology (BCH) domain, is associated with favorable prognosis in human neuroblastomas," *Oncogene*, vol. 25, No. 13, pp. 1931-1942, published Mar. 2006.
Mousley C.J. et al., "The Sec14-superfamily and the regulatory interface between phospholipid metabolism and membrane trafficking," *Biochimica Biophysica et Acta*, vol. 1771, pp. 727-736, published Jun. 2007.
Qin W. et al., "BNIPL-2, a novel homologue of BNIP-2, interacts with Bcl-2 and Cdc42GAP in apoptosis," *Biochemical and Biophysical Research Communications*, vol. 308, pp. 379-385, published Aug. 22, 2003.
Rain J.C. et al., "The protein-protein interaction map of *Helicobacter pylori*," *Nature*, vol. 409, pp. 211-215, published Jan. 11, 2001.
Shang X. et al., "Concerted Regulation of Cell Dynamics by BNIP-2 and Cdc42GAP Homology/Sec14p-like, Proline-rich, and GTPase-activating Protein Domains of a Novel Rho GTPase-activating Protein, BPGAP1," *The Journal of Biological Chemistry*, vol. 278, No. 46, pp. 45903-45914, published Nov. 14, 2003.
Sirokmány G. et al., "Sec14 Homology Domain Targets p50RhoGAP to Endosomes and Provides a Link between Rab and Rho GTPases," *The Journal of Biological Chemistry*, vol. 281, No. 9, pp. 6096-6105, published Mar. 3, 2006.
Tassabehji M. et al., "Waardenburg syndrome type 2 caused by mutations in the human microphthalmia (*MITF*) gene," *Nature Genetics*, vol. 8, pp. 251-255, published 1994.
Vegeto E. et al., "Estrogen and progesterone induction of survival of monoblastoid cells undergoing TNF-α-induced apoptosis," *Faseb J*, vol. 13, pp. 793-803, published 1999.
Vojtek A. et al., "Ras-Raf Interaction: Two-Hybrid Analysis," *Methods in Enzymology*, vol. 255, pp. 331-342, published 1995.
Yu C.E. et al., "Positional Cloning of the Werner's Syndrome Gene," *Science*, vol. 272, pp. 258-262, published Apr. 12, 1996.
Zhou Y.T. et al., "BNIP-2 induces cell elongation and membrane protrusions by interacting with Cdc42 via a unique Cdc42-binding motif within its BNIP-2 and Cdc42GAP homology domain," *Experimental Cell Research*, vol. 303, pp. 263-274, published Feb. 15, 2005.

*Primary Examiner* — Amy Bowman
(74) *Attorney, Agent, or Firm* — John P. White; Cooper & Dunham LLP

(57) ABSTRACT

The present invention concerns the use of a polypeptide comprising a sequence having at least 90% identity with all or part of BNIPXLβ, for cosmetic or therapeutic applications, in the treatment or prevention of premature canities in humans, said portion comprising at least 30 amino acids, as well as the use, for the same purpose, of a molecule comprising a RNAi sequence having at least 90% identity with all or part of the cDNA sequence of BNIPXLβ, said part comprising at least 18 nucleotides.
The invention also concerns methods for screening molecules modulating the expression of a gene coding for BNIPXL-beta and molecules modulating the activity of the BNIPXL-beta polypeptide, in order to identify an agent for use for cosmetic or therapeutic purposes in the field of pigmentation. The invention also encompasses various uses of molecules which may be identified by these methods.

4 Claims, 3 Drawing Sheets

SEQ ID N°1

MSKLTLSEGHPETPVDGDLGKQDICSSEASWGDFEYDVMGQNIDEDLLREPEHFLYGGDPPLEE

DSLKQSLAPYTPPFDLSYITEPAQSAETIEEAGSPEDESLGCRAAEIVLSALPDRRSEGNQAET

KNRLPGSQLAVLHIREDPESVYLPVGAGSNILSPSNVDWEVETDNSDLPAGGDIGPPNGASKEI

SELEEEKTIPTKEPEQIKSEYKEERCTEKNEDRHALHMDYILVNREENSHSKPETCEERESIAE

LELYVGSKETGLQGTQLASFPDTCQPASLNERKGLSAEKMSSKSDTRSSFESPAQDQSWMFLGH

SEVGDPSLDARDSGPGWSGKTVEPFSELGLGEGPQLQILEEMKPLESLALEEASGPVSQSQKSK

SRGRAGPDAVTHDNEWEMLSPQPVQKNMIPDTEMEEETEFLELGTRISRPNGLLSEDVGMDIPF

EEGVLSPSAADMRPEPPNSLDLNDTHPRRIKLTAPNINLSLDQSEGSILSDDNLDSPDEIDINV

DELDTPDEADSFEYTGHEDPTATKDSGQESESIPEYTAEEEREDNRLWRTVVIGDQEQRIDMKV

IEPYRRVISHGGLRGYYGDGLNAIIVFAACFLPDSSRADYHYVMENLFLYVISTLELMVAEDYM

IVYLNGATPRRRMPGLGWMKKCYQMIDRRLRKNLKSFIIVHPSWFIRTILAVTRPFISSKFSSK

IKYVNSLSELSGLIPMDCIHIPESIIKY

Figure 1:
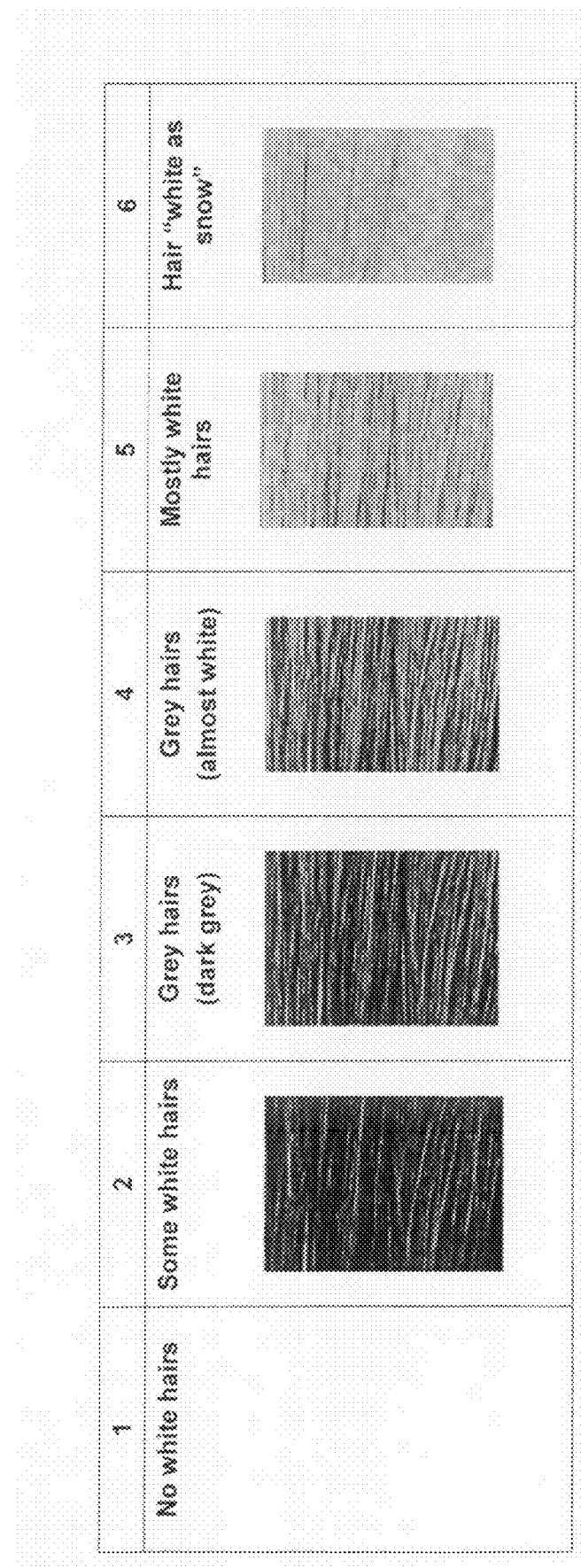

FIG. 2A gctttgtttgatggtgatccacatttatccacagagaatcctgccttggttcctgatgctttgc
tagcctcagacacttgtctggatataagcgaagctgcctttgaccacagtttcagcgatgcctc
aggtctcaacacatccacgggaacaatagatgac**ATGAGTAAACTGACATTATCCGAAGGCCAT
CCGGAAACGCCAGTTGATGGGGACCTAGGGAAGCAAGATATCTGCTCATCTGAAGCCTCGTGGG
GTGATTTTGAATATGATGTAATGGGCCAGAATATCGATGAAGATTTACTGAGAGAGCCTGAACA
CTTCCTGTATGGTGGTGACCCTCCTTTGGAGGAAGATTCTCTGAAGCAGTCGCTGGCACCGTAC
ACACCTCCCTTTGATTTGTCTTATATCACAGAACCTGCCCAGAGTGCTGAAACAATAGAGGAAG
CTGGGTCTCCAGAGGATGAATCTCTGGGATGCAGAGCAGCAGAGATAGTGCTTTCTGCACTTCC
TGATCGAAGAAGTGAGGGAAACCAGGCTGAGACCAAAAACAGACTGCCTGGATCCCAGCTGGCT
GTGCTGCATATTCGTGAAGACCCTGAGTCCGTTTATTTGCCGGTAGGAGCAGGCTCCAACATTT
TGTCTCCATCAAACGTTGACTGGGAAGTAGAAACAGATAATTCTGATTTACCAGCAGGTGGAGA
CATAGGACCACCAAATGGTGCCAGCAAGGAAATATCAGAATTGGAAGAAGAAAAAACAATTCCT
ACCAAAGAGCCTGAGCAGATAAAATCAGAATACAAGGAAGAAAGATGTACAGAGAAGAATGAAG
ATCGTCATGCACTACACATGGATTACATACTTGTAAACCGTGAAGAAAATTCACACTCAAAGCC
AGAGACCTGTGAAGAAAGAGAAAGCATAGCTGAATTAGAATTGTATGTAGGTTCCAAAGAAACA
GGGCTGCAGGGAACTCAGTTAGCAAGCTTCCCAGACACATGTCAGCCAGCCTCCTTAAATGAAA
GAAAAGGTCTCTCTGCAGAGAAAATGTCTTCTAAAAGCGATACGAGATCATCTTTTGAAAGCCC
TGCACAAGACCAGAGTTGGATGTTCTTGGGCCATAGTGAGGTTGGTGATCCATCACTGGATGCC
AGGGACTCAGGGCCTGGGTGGTCCGGCAAGACTGTGGAGCCGTTCTCTGAACTCGGCTTGGGTG
AGGGTCCCCAGCTGCAGATTCTGGAAGAAATGAAGCCTCTAGAATCTTTAGCACTAGAGGAAGC
CTCTGGTCCAGTCAGCCAATCACAGAAGAGTAAGAGCCGAGGCAGGGCTGGCCCGGATGCAGTT
ACCCATGACAATGAATGGGAAATGCTTTCACCACAGCCTGTTCAGAAAAACATGATCCCTGACA
CGGAAATGGAGGAGGAGACAGAGTTCCTTGAGCTCGGAACCAGGATATCAAGACCAAATGGACT
ACTGTCAGAGGATGTAGGAATGGACATCCCCTTTGAAGAGGGCGTGCTGAGTCCCAGTGCTGCA
GACATGAGGCCTGAACCTCCTAATTCTCTGGATCTTAATGACACTCATCCTCGGAGAATCAAGC
TCACAGCCCCAAATATCAATCTTTCTCTGGACCAAAGTGAAGGATCTATTCTCTCTGATGATAA
CTTGGACAGCCCAGATGAAATTGACATCAATGTGGATGAACTTGATACCCCCGATGAAGCAGAT
TCTTTTGAGTACACTGGCCATGAAGATCCCACAGCCACCAAAGATTCTGGCCAAGAGTCAGAGT
CTATTCCAGAATATACGGCCGAAGAGGAACGGGAGGACAACCGGCTTTGGAGGACAGTGGTCAT
TGGAGACCAAGAGCAGCGCATTGACATGAAGGTCATCGAGCCCTACAGGAGAGTCATTTCTCAC
GGAGGACTTAGAGGATACTATGGGGACGGTCTAAATGCCATCATTGTGTTTGCCGCCTGTTTTC
TGCCAGACAGCAGTCGGGCGGATTACCACTATGTCATGGAAAATCTTTTCCTATATGTAATAAG
TACTTTAGAGTTGATGGTAGCTGAAGACTATATGATTGTGTACTTGAATGGTGCAACCCCAAGA
AGGAGGATGCCAGGGCTAGGCTGGATGAAGAAATGCTACCAGATGATTGACAGACGGTTGAGGA
AGAATTTGAAATCATTCATCATTGTTCATCCATCTTGGTTCATCAGAACAATCCTTGCTGTGAC
ACGACCTTTTATAAGTTCAAAATTCAGCAGTAAAATTAAATATGTCAATAGCTTATCAGAACTC
AGTGGGCTGATCCCAATGGATTGCATCCACATTCCAGAGAGCATCATCAAATATTGA**cttgaag
ctgaaagaaaagccttagttggccatgctggaagaag

SEQ ID N°2

FIG. 2B

USES OF BNIPXL-BETA IN PREMATURE CANITIES

This application claims priority of French Patent Application No. 08/02435, filed Apr. 30, 2008, the entire contents of which are hereby incorporated by reference into this application.

Rectifying or nullifying the effects of ageing as far as possible is a preoccupation of ever-increasing importance. In this context, white hairs, which are deemed to be unsightly, are very often caused to disappear using coloring treatment shampoos. Clearly, however, although that technique has proved effective in nullifying the effects of the phenomenon, it has no effect on its causes. For this reason, that solution is temporary and has to be frequently renewed.

Hair turns white (canities or hair greying) due to the gradual disappearance of melanocytes from the hair follicle (Commo S, Gaillard, O & Bernard, B A, 2004). This process affects both the melanocytes of the pigmentation unit located at the base of the follicle and directly responsible for the pigmentation of the fiber, as well as progenitor melanocytes located in the distal portion of the outer sheath of the hair follicle which act as a reservoir from which the pigmentation unit is renewed on each hair cycle (Common S and Bernard B A, 2000).

Although the gradual disappearance of melanocytes appears to be linked to the absence of expression of the enzyme dopachrome tautomerase (Commo S, Gaillard O, Thibaut S & Bernard B A, 2004, patents FR-2 840 530, FR-2 840 531, FR-2 863 484), the inventors have elected to explore the appearance of white hairs, or canities, from a completely novel angle, that of genetics. They sought to identify other genes which may be associated with premature canities using a global genetic approach.

Exploring canities from a genetic viewpoint means that the underlying mechanisms of depigmentation can be identified. This also allows the genes which are involved in canities to be identified. This identification opens the door to many applications in the field of hair care, whether cosmetic, therapeutic or diagnostic.

To this end, the inventors have elected to concentrate their research in the first instance on premature canities (PC), i.e. the appearance of white hair very early on in life, also known as premature hair greying, the hereditary nature of which is known and has been linked to certain autoimmune diseases. In order to explore canities genetically, a segregation study was carried out on DNA from families for whom canities appears very early on in life. In order to guarantee the best chances of success for this gene hunt, the PC phenotype was attributed only to those individuals who had white hair before the age of 25 and for whom half the hair of the head was gray at 30 years of age. Twelve families were retained for participation in a linkage study.

The results of these studies have allowed the inventors to define, in the first place, chromosomal and/or genomic zones comprising the genes which are most probably involved in canities. Five loci were thus identified on chromosomes 3, 5 and 11 (patent applications FR-2 842 105 and WO-04/007764) and on chromosomes 6 and 9 (patent applications FR-2 842 104, FR-2 853 532, FR-2 865 217 and WO-04/007742).

Of the genes associated with premature canities, the gene DDX31 (GI: 20336296; accession n° NM_022779) has been proposed as a putative gene linked to premature canities, located at 9q34 and described in L'Oreal's patent applications FR-2 853 532 and FR-2 865 217. DDX31, DEAD box protein 31, is a probable ATP-dependent RNA helicase belonging to the DEAD box family of helicases.

In order to initially explore the role of DDX31 in the premature canities process, the inventors sought to identify possible protein partners susceptible of interacting with DDX31 using a two-hybrid approach in the yeast system.

Surprisingly and unexpectedly, the inventors discovered that BNIPXL-beta (BCl2/adenovirus E1B 19 kDa protein-interacting protein 2) is a pray of DDX31, preferably of the long form of DDX31. The confidence score in the interaction is particularly good.

The various functions of BNIPXL-beta are still relatively unknown. This protein is produced by alternative splicing of KIM0367 (alias: BCH motif-containing molecule at the C-terminal region 1, BNIP2 motif-containing molecule at the C-terminal region 1; accession n°: O58A63; GI: 125987727).

On account of domain homology (CRAL-TRIO or Sec14 domain; domain present in BNIP2) BNIPXL-beta is thought to be involved in the transport and metabolism of phospholipids; to have a pro-apoptotic function linked to an interaction with bcl2; and to participate in cellular traffic; it may play a role in the formation of membrane protusions (Machida et al, 2006; Zhou et al, 2005; Shang et al, 2003; Qin et al, 2003; Belcredito et al, 2001; Sirokmany et al, 2006; Mousley et al, 2007).

The interaction between DDX31 and BNIPXL-beta is thus most probably important in vesicular traffic, hence its role in the migration and transfer of melanosomes and thus its involvement in canities including premature canities.

In this application, the following terms have the following meanings in particular:

Degree of identity: the degree of identity between two sequences (protein or nucleic) is determined by aligning the two sequences in order to maximize the points of agreement while minimizing the gaps; it is obtained by dividing the number of common amino acids or nucleic acids by the length of the longest of the two sequences.

RNAI: RNA interference; a molecule of RNA which is capable of targeting a particular sequence in a RNA molecule and of guiding cleavage of that RNA at a predetermined site in the target sequence. The RNA molecule capable of cleaving by RNA interference is correspondingly named interfering RNA or RNAi. When this reaction takes place in a cell and the cleaved RNA is messenger RNA (mRNA), cleavage of the mRNA molecule then leads to degradation of the molecule, thereby preventing any subsequent steps, such as translation of mRNA into protein. Depending on the type of RNAi, the target sequence is either the complementary sequence of the interfering RNA (in particular siRNA) or a quasi-complementary sequence of the interfering RNA, however with some non-concordant sequences (in particular miRNA).

siRNA: short interfering RNA: a double stranded RNA sequence comprising approximately 21 to 23 nucleotides (Dykxhoorn et al, Nature Reviews 2003, vol 4, p. 457). The siRNA may be derived from cleavage of double stranded RNA with larger dimensions by a protein termed a dicer. The siRNA produced is then integrated into a multiprotein inhibiting complex induced by RNA (RISC, RNA-inducing silencing complex). The target mRNA is cleaved at a single site in the center of the duplex region formed between the siRNA (which acts as a guide) and target mRNA, 10 nucleotides from the 5' end of the siRNA.

In order to obtain siRNA in a cell, several methods may be envisaged:
1. it is possible to directly introduce siRNA obtained by chemical synthesis into a cell; in this case, the action of the dicer is circumvented;

2. it is also possible to envisage introducing into the cell large double strand RNA fragments which are then cleaved into siRNA by the dicer protein;
3. it is possible to introduce or to express in the cell a RNA hairpin duplex, for example a shRNA (small or short hairpin RNA) which is then cleaved by the dicer protein into siRNA.

Polynucleotide fragment means any molecule resulting from the linear concatenation of at least two nucleotides, said molecule possibly being monocatenary, bicatenary or tricatenary. It may thus be a double stranded DNA molecule, a single stranded DNA molecule, RNA, a duplex between a single stranded DNA-RNA, a DNA-RNA triplex or any other combination. The polynucleotide fragment may be natural, isolated, recombinant or synthetic. When the polynucleotide fragment includes complementary strands, the complementarity is not necessarily perfect, but the affinity between the various stands is sufficient to allow a stable Watson Crick type bond to be established between the two strands.

Although the base pairing is preferably of the Watson-Crick type, other types are not excluded, such as Hoogsteen or reverse Hoogsteen type pairing.

In a first aspect, the present invention concerns the BNIPXLβ protein, or a portion of BNIPXLβ, for a therapeutic or cosmetic application, in particular for the treatment or prevention of premature canities in humans. Because of its interaction with DDX31 in a process involved in premature canities, this protein is itself connected with canities, especially premature canities.

The sequence of the BNIPXLβ protein is illustrated in FIG. 2A and corresponds to the sequence SEQ ID NO: 1. A "portion" of BNIPXLβ as used in the context of the present application is a polypeptide comprising at least 25 consecutive amino acids of the BNIPXLβ sequence. Preferably, a portion of BNIPXLβ comprises at least 30 consecutive amino acids of SEQ ID NO: 1.

In the context of the present description, the term "cosmetic" means any application which is intended only for aesthetic modification and has no therapeutic application.

The invention also concerns a polypeptide comprising the sequence of BNIPXLβ or comprising a portion of BNIPXLβ, said portion being as defined above, for a therapeutic or cosmetic application.

The invention also concerns any polypeptide comprising a region having at least 90% identity with BNIPXLβ or with a portion of BNIPXLβ, for a therapeutic application especially in the field of premature canities. Said portion of BNIPXLβ comprises at least 25 amino acids, preferably at least 30 amino acids.

The polypeptide described thus comprises a region the sequence of which shares a high percentage of identity with BNIPXLβ or with a portion of BNIPXLβ, but it may also include other sequences in addition to that mentioned above, at the N-terminal or the C-terminal end, or at both.

Preferably, in the region of the polypeptide having a high percentage identity with BNIPXLβ, or with a portion of BNIPXLβ, the percentage identity is more than 90%, preferably more than 95% or even 98%.

In accordance with a preferred embodiment, said polypeptide comprises a portion of the BNIPXLβ protein, said portion comprising at least 25 amino acids, or even 30 amino acids or more.

Preferably again, the polypeptide comprises a sequence sharing a high percentage identity with a portion of BNIPXLβ of at least 40 or even 50 consecutive amino acids, or even 75 or 100, of the 732 amino acids of the BNIPXLβ protein. Preferably, the portion of BNIPXLβ is a portion corresponding to a domain having biological importance, for example a binding site for a protein partner. There exist programs which are known to the skilled person for determining domains of particular interest in the sequence SEQ ID NO: 1.

The therapeutic or cosmetic applications mentioned are in all fields, more particularly that of hair therapy, especially the treatment of canities including premature canities.

The present invention also concerns the use of BNIPXLβ, a portion of BNIPXLβ as described above or a polypeptide as described, for the preparation of a medicament for the treatment or prevention of canities in man, preferably premature canities.

The invention also concerns a therapeutic or cosmetic method for the treatment or prevention of canities in humans, preferably premature canities, making use of BNIPXLβ, a portion of BNIPXLβ as described above or a polypeptide as described.

Further, the inventors have determined the importance of the interaction between DDX31 and BNIPXLβ and thus the beneficial effect of a reduction in the level of expression of BNIPXLβ which may be obtained by RNAi. Such a beneficial effect may in particular be in the premature canities phenotype.

Thus, the present invention also concerns a molecule comprising a RNAi sequence having at least 90% identity with all or part of the mRNA sequence corresponding to BNIPXLβ, for therapeutic or cosmetic use in humans, said portion comprising at least 18 nucleotides. Preferably, the part in question comprises at least 20, 25 or even 30 nucleotides.

Preferably, the therapeutic application consists in the treatment or prevention of canities, more particularly premature canities.

The mRNA sequence is equivalent to the cDNA sequence of BNIPXLβ illustrated in FIG. 2B as sequence SEQ ID NO: 2.

In the context of the present application, during determination of the degree of identity between a RNA sequence and a DNA sequence, the guanine of the RNA is considered to be equivalent to the thymine of DNA; as a consequence, a given DNA sequence and the RNA sequence derived from that DNA sequence by replacing T with G has 100% identity in the context of the present invention.

The RNAi mentioned above preferably consists of a fragment of double stranded RNA, the two base-paired sequences possibly being either within the same molecule, thereby forming a hairpin structure, or within two distinct single stranded molecules.

The molecule including the RNAi sequence may thus be constituted by a single folded RNA fragment or by two RNA molecules. This molecule may include other sequences, RNA or DNA, single or double stranded, on the 3', 5' side or the two sides of the pairing sequences, or also between the pairing sequences, for example in the loop when the molecule is constituted by a single pairing RNA molecule.

The RNAi mentioned may be a siRNA or a shRNA. Preferably, the molecule comprising the RNAi sequence is such that it may be cleaved by the dicer protein in order to provide a shRNA interfering with the mRNA of BNIPXLβ.

The present invention also concerns the use of a molecule as defined above, for the preparation of a drug for the treatment or prevention of premature canities in man.

The invention also concerns screening methods, in particular a method for screening molecules modulating the expression of the gene coding for BNIPXL-beta in order to identify an agent for a use for cosmetic or therapeutic purposes, in the field of pigmentation.

A gene coding for the BNIPXLβ protein (or BNIPXL-beta) is, for example, the BMMCC1 gene (synonyms: BNIPXL, KIM0367), one of its accession numbers in the databases being ENSG00000106772 (Ensemble gene ID). From this gene, by alternative splicing, at least three variants result; canonical isoform 1 corresponds to a polypeptide with 2724 amino acids, isoform 3 corresponds to BNIPXL-beta, a polypeptide with 732 amino acids being essentially distinguished from canonical isoform 1 by the absence of amino acids 1-1959.

Gene expression may in particular be modulated by modulating its transcription or translation.

Screening using the method of the invention means that molecules which prevent, inhibit, delay or retard transcription and/or translation of the gene, or which increase or reduce the level or transcription and/or translation of the gene, or which modify the proportions of the various isoforms in the expression of the BMMCC1 gene, can be identified. One molecule which is susceptible of being identified by the screening method of the invention is thus a molecule which considerably reduces the expression of the isoform 3 to the advantage of isoform 1 of the BMMCC1 gene.

The terms "increase", "reduce", "modulate", "inhibit" or "modulate" should be understood to mean significant variations in amplitude, i.e. much greater than the noise and inaccuracies of the measurement, and thus significant variations from a statistical viewpoint, of greater than the standard deviation.

It should be noted that a screening method of the invention is specially designed to be carried out ex vivo, for example in cell cultures. Preferably, it is carried out in vitro. If necessary, this method may also be carried out in vivo, although this is not the recommended implementation.

A method of the invention preferably comprises the following steps:
    bringing the molecule to be tested into the presence of the gene coding for BNIPXL-beta, under conditions allowing expression of said gene, in the absence of the test molecule; and
    detecting a variation in the degree of expression of said gene or in the nature of the expression products of said gene, due to the presence of the test molecule.

The term "nature of the expression products" as explained above, for example, means the respective proportions of the various isoforms, or the appearance or disappearance of a given isoform.

The test molecules may be of any chemical nature. Preferably, they are small molecules which can pass through cell walls. Particular preferred molecules are artificial chemical molecules essentially comprising the elements C, H, O, N, possibly with the elements Cl or F. Alternatively, the test molecules may be biological molecules such as proteins, polypeptides, antibodies, fragments of antibodies, RNAi, antisense RNA, ribozymes, aptamers or molecules which can be synthesized in a eukaryotic cell.

Particularly preferred test molecules are proteins, RNAi, ribozymes or antisense RNA targeting BNIPXLβ or targeting the gene coding for BNIPXL-beta, for example antibodies directed against BNIPXLβ or RNAi's against the mRNA corresponding to BNIPXLβ.

The conditions allowing expression of said gene involve the presence of various enzymes which are required such as RNA polymerase, nucleotides and amino acids, ribosomes, or any other structure allowing the transcription and translation of said gene. These various elements are naturally found in cells as a general rule and must be added if the method is carried out in vitro.

A variation in the level of expression of said gene or in the nature of the expression products of said gene following addition of the test molecule may be detected using any means which are considered to be appropriate by the skilled person. It may be by assay, for example enzymatic assay, or by the use of detection means based on immunology (immunoassay), or using any other known means based, for example, on the functional properties of the expression products, their physico-chemical properties (isoelectric point, molecular mass, etc), immunological, or others.

The proportions of the various isoforms may be determined using the same principle. In particular, it may employ various antibodies which specifically recognize a given isoform and which do not interact with the other isoforms.

In the context of the present invention, it should be noted that the particularly desired modulation of expression is inhibition of expression, in particular inhibition of transcription or translation of the BMMCC1 gene, or a reduction in the proportion of isoform 3 from among the expression products of the BMMCC1 gene.

Inhibition may be complete or partial; in all cases, it involves a reduction in the production of the BNIPXLβ polypeptide from the BMMCC1 gene, said reduction being statistically significant. Preferably, it is a reduction in the level of expression of BNIPXLβ from the BMMCC1 gene of at least 20%, preferably at least 35%, or even 50%, and more preferably a reduction of more than 60%.

A method as described above may include one or more additional steps, which may be anterior, posterior and/or intermediate. In particular, in the case in which the method has allowed the detection of a molecule which significantly modulates expression of the BMMCC1 gene, it is envisaged that one proceeds to a step for identifying the molecule then producing it in larger quantities. It is also possible to envisage testing various other molecules with a structure very close to that which can modulate expression of said gene.

The present invention also concerns a method for screening molecules which are capable of modulating the activity of the BNIPXL-beta polypeptide, for the identification of an agent for use for cosmetic or therapeutic purposes, in the field of pigmentation. The test molecules may have any nature as explained above, they may be completely artificial or naturally present in the biological systems.

In similar manner to the above screening method, this screening method is preferably carried out ex vivo, and preferably in vitro, although an in vivo method is not to be excluded.

The term "modulation of activity" means any significant modification of the parameters defining the activity, especially the nature of the target and the rate of reaction in the case of enzymatic activity and the affinity and avidity in the case of an interaction.

The "significant" nature of a modification has already been explained above when the parameter which is modified can be quantified.

A screening method as described preferably comprises the following steps:
    bringing the test molecule and the BNIPXL-beta polypeptide into contact under conditions which can determine the activity of said polypeptide in the absence of the test molecule; and
    detecting a variation in the activity of said polypeptide due to the presence of the test molecule.

The conditions which mean that the activity of BNIPXLβ can be detected involve in particular the presence of various partners acting with BNIPXLβ in the context of this activity, as well as suitable physico-chemical conditions such as temperature, pH, or the oxidizing or reducing nature of the medium.

These various elements and conditions are found naturally in cells as a general rule, or in at least some thereof, and must be added or adapted if the method is carried out in vitro.

The activity a variation of which is to be detected may, for example, be the interaction with DDX31, preferably with the long form of DDX31.

The polypeptide BNIPXL-beta used in the context of this method is a polypeptide consisting of the sequence SEQ ID NO: 1 and preferably having undergone the same post-translational modifications as the protein BNIPXLβ when it is produced in vivo in human cells, especially with the same glycosylation profile. However, in the context of the method of the invention, the use of polypeptides having a sequence which is not completely identical to SEQ ID NO: 1 may be envisaged, either because it is longer but contains SEQ ID NO: 1, or because it is shorter but it includes at least 100 consecutive amino acids of SEQ ID NO: 1, or because it includes a sequence with at least 90% identity with all or part of SEQ ID NO: 1, said part having at least 50 amino acids, preferably at least 100 amino acids, preferably with at least 95% identity, the differences with respect to SEQ ID NO:1 possibly being cumulative. The use of a polypeptide with post-translational modifications which are not identical with those of the BNIPXLβ protein produced in a human cell may also be envisaged.

In the case in which the screening method of the invention is carried out with a protein having several modifications with respect to the natural human BNIPXLβ protein, the skilled person will know that it is important in this case to confirm the modulation observed by this method by repeating the method with the natural human BNIPXLβ protein.

Detecting a variation in the activity of said polypeptide following addition of the test molecule may be carried out using any means which is considered appropriate by the skilled person. It is possible to detect a parameter linked directly to the activity of said polypeptide (for example, the appearance of a product resulting directly from the enzymatic activity of BNIPXLβ) or a parameter linked indirectly to this activity, especially in the case of triggering enzymatic cascades.

It may concern assay, for example enzymatic assay, of the reaction product, or concern the use of detection means based on immunology (immunoassay) of a complex formed between said polypeptide and its target, its target possibly being DDX31, or by any other known means based, for example, on the functional properties of the product resulting from the activity of the polypeptide, i.e. on the physico-chemical properties (isoelectric point, molecular mass, etc), immunological properties, or other properties of a polypeptide or complex resulting from the activity of BNIPXLβ.

In accordance with a preferred embodiment of this method of the invention, the desired modulation of the activity of BNIPXLβ is inhibition, total or partial, of that activity.

Partial inhibition is preferably inhibition by at least 10% of the activity of said polypeptide by reference to the level of activity before adding the test molecule.

Preferably, the activity is modulated by sequestration of said polypeptide. In this manner, the polypeptide BNIPXLβ is no longer available for another interaction other than that with the sequestrating molecule, or sequestrated in a compartment of the cell where its binding partners are absent. The skilled person will be able to define, based on the structure and sequence of BNIPXLβ, the molecules or conditions which are susceptible of having the desired sequestration effect.

In order to carry out the method of the invention as described, it is particularly advantageous to use, as test molecules, antibodies directed against the polypeptide BNIPXL-beta or against a portion thereof. Programs which can define which portion of BNIPXL-beta is susceptible of being immunogenic and thus of obtaining the antibody are available. Further, the antibody technique, monoclonal or polyclonal, is now well developed; it also concerns the humanization of murine antibodies, readily enabling the skilled person to produce and rapidly test a large number of molecules from this category in a method of the invention.

As mentioned above, the screening methods described in the invention may advantageously include one or more steps in addition to those already mentioned, in particular anterior, posterior and/or intermediate steps.

For the two types of screening method described, the aim is the identification, from among the test molecules, of an agent for use for cosmetic or therapeutic purposes, i.e. an agent for cosmetic or therapeutic use, in the field of pigmentation. The pigmentation in question is preferably the pigmentation of the hair and nails, most preferably that of the hair of the head.

The present invention also concerns various uses, in particular the use of agents which have been screened by the methods described above, for cosmetic purposes in the field of pigmentation or for therapeutic purposes, of treatment or prevention, in the field of pigmentation, as well as therapeutic and cosmetic methods, in the filed of pigmentation, making use of agents which have been screened by the methods described above.

The present invention also concerns the use of an agent modulating the expression of a gene coding for BNIPXL-beta, for cosmetic purposes in the field of pigmentation, as well as the use of an agent modulating the expression of a gene coding for BNIPXL-beta for the manufacture of a drug for therapeutic use in the field of pigmentation and therapeutic and cosmetic methods, in the filed of pigmentation, making use of an agent modulating the expression of a gene coding for BNIPXL-beta.

The definition of what is meant by the terms "modulate expressions" has already been given in the context of screening methods in accordance with the invention. This term in particular covers the modulation of transcription and the modulation of translation of the gene in question. The modulation is preferably a reduction or inhibition, total or partial, of said expression, transcription or translation, of the gene.

An "agent" corresponds to any type of chemical, natural or artificial molecule. Particularly preferred agents are those which are susceptible of being identified or which have been identified using a screening method of the invention as described above, i.e. a method for screening a molecule which modulates the expression of a gene coding for BNIPXL-beta.

The present application also concerns an agent modulating the expression of a gene coding for BNIPXL-beta for a therapeutic use in the field of pigmentation. The scope of the present invention also includes uses of an agent modulating the activity of a polypeptide derived from translation of a gene coding for BNIPXL-beta, for cosmetic purposes, in the field of pigmentation, as well as the use of an agent modulating the activity of a polypeptide derived from translation of a gene coding for BNIPXL-beta, for the production of a drug for a therapeutic use in the field of pigmentation. The invention also concerns therapeutic and cosmetic methods, in the filed of pigmentation, making use of an agent modulating the activity of a polypeptide derived from translation of a gene coding for BNIPXL-beta.

Preferably, a polypeptide derived from translation of a gene coding for BNIPXL-beta is BNIPXL-beta.

The definition of that which is to be understood by the terms "modulate the activity" has already been given in the context of screening methods in accordance with the invention. The modulation is preferably a reduction, or even total or partial inhibition of said activity.

An agent modulating the activity of a polypeptide derived from translation of a gene coding for BNIPXL-beta, may be any type of chemical, natural or artificial molecule. Particularly preferred agents are those which are capable of being identified or which have been identified by a screening method of the invention as described above, i.e. a method for screening molecules capable of modulating the activity of the polypeptide BNIPXL-beta.

The present application also concerns an agent modulating the activity of BNIPXL-beta, for a therapeutic use in the field of pigmentation.

In accordance with a further aspect, the invention is also directed towards the use of at least one polynucleotide fragment comprising at least 18 consecutive nucleotides the sequence of which corresponds to all or a portion of the gene coding for BNIPXL-beta or a transcript of BNIPXL-beta, for cosmetic purposes, in the field of pigmentation.

The polynucleotide fragment referred to in the context of the invention corresponds to a fragment of a chromosome. This fragment has a minimum length of 18 nucleotides, and a maximum length which may be up to the total length of the gene coding for BNIPXLβ. Preferably, the fragment contains more than 18 nucleotides. A particularly preferred length is in the range 18 to 10000 nucleotides, preferably in the range 30 to 8000 nucleotides.

In accordance with preferred embodiments of the invention, reference may be made to fragments with a length in the range 30 to 5000 nucleotides, preferably in the range 50 to 3000 nucleotides, for example in the range 100 to 2000 nucleotides, or in the range 200 to 1000 nucleotides.

The present inventors have demonstrated the interaction between the polypeptide BNIPXLβ and a polypeptide derived from translation of the DDX31 gene, this interaction being involved in the premature canities phenomenon. The present invention thus also concerns methods for screening molecules modulating the interaction between a BNIPXL-beta polypeptide and a polypeptide derived from translation of the DDX31 gene, allowing identification of an agent for use for cosmetic or therapeutic purposes in the field of pigmentation.

The various cosmetic or therapeutic uses or methods in the context of the present invention have already been detailed as well as what is meant by the "field of pigmentation", i.e. principally the pigmentation of the hair and nails, preferably the hair of the head.

The term "modulation of the interaction" means a modification of the parameters characterizing this interaction, and particularly the affinity. A "modulation" is a significant variation from a statistical viewpoint.

A polypeptide derived from translation of the DDX31 gene corresponds to the long form (1-851) or short form (1-585) of DDX31. Preferably, it is the long form of DDX31.

According to a preferred embodiment, said modulation is a disruption of the association between the two polypeptides, preferably total disruption.

In accordance with another implementation of the screening method, the desired modulation is a modification of the association constant between the two polypeptides. As before, the term "modification of the association constant" means a significant variation in this constant from a statistical viewpoint.

Preferably, by carrying out the method, it is possible to identify an agent which is a competitive inhibitor of the association between the two polypeptides.

By dint of this method, it is thus possible to identify agents which modulate the interaction between BNIPXLβ and a polypeptide derived from translation of the DDX31 gene, for example by binding to BNIPXLβ and thereby preventing its interaction with said polypeptide, or by binding to the polypeptide derived from translation of the DDX31 gene and thereby preventing its interaction with BNIPXLβ.

The present invention also encompasses agents identified by the method described above.

An agent which modulates the interaction between BNIPXL-beta and a polypeptide derived from translation of the DDX31 gene as defined in the context of this invention may be envisaged in a cosmetic or therapeutic application or method, preferably in the field of pigmentation. Such an agent may be identifiable or identified by the screening method described above.

The invention also concerns the use of an agent modulating the interaction between BNIPXL-beta and a polypeptide derived from translation of the DDX31 gene, for the manufacture of a drug for therapeutic use in the field of pigmentation.

Preferred agents which are capable of modulating said interaction are antibodies or antibody fragments, preferably directed against BNIPXLβ or against a polypeptide derived from translation of the DDX31 gene. Such antibodies may be monoclonal or polyclonal; preferably, they are monoclonal antibodies.

For all use, methods s or applications of the invention in the field of cosmetics, the polypeptide, the molecule, the agent or the polynucleotide fragment which is used, may be packaged into various appropriate forms, alone or in combination with other agents. In particular, preferred forms are intended to be used in local applications and they concern creams, lotions, gels, emulsions, pomades and shampoos. Other forms can be envisaged for the uses of the invention, in particular as tablets for oral administration.

Of the various cosmetic aims of the present invention, one particularly preferred field is that of pigmentation. Pigmentation may be that of the skin or even the hair and nails. It may concern the color of the pigmentation, such as the absence of pigmentation; the invention also concerns problems affecting the quality and intensity of pigmentation.

In particular, the subject matter of the invention concerns the use of at least one polypeptide, molecule, agent or polynucleotide fragment as defined above, to prevent and/or limit and/or stop the development of canities.

The subject matter of the invention also pertains to the use of at least one polypeptide, molecule, agent or polynucleotide fragment as defined above to encourage the natural pigmentation of gray hair and/or body hair.

The present invention also pertains to a method for the cosmetic treatment of canities, characterized in that a composition comprising at least one polypeptide, molecule, agent or polynucleotide fragment as defined above is applied to the zone to be treated.

The invention also concerns a cosmetic treatment method intended to encourage the natural pigmentation of gray or white hair and/or body hair, characterized in that a composition comprising at least one polypeptide, molecule, agent or polynucleotide fragment as defined above is applied to the zone to be treated.

The zones to be treated may, for example and without limitation, be the scalp, eyebrows, moustache, beard and/or any hairy zone of the body.

More particularly, the methods for the treatment of canities and natural pigmentation of gray or white hair and/or body hair consists of applying a composition comprising at least one polypeptide, molecule, agent or polynucleotide fragment as defined above.

Regarding the various uses or therapeutic applications of the invention, it should be noted that disorders concerning the pigmentation system, whether that of the skin or the hair and nails, may have grave consequences as regards the health of the affected individuals. Skin pigmentation acts as a protective barrier to light in particular; individuals suffering from albinism do not have protection from sunlight which constitutes a major danger to them. Other disorders involving pigmentation are also a concern of the present invention.

In the context of therapeutic and cosmetic uses or methods which tend to modify a characteristic of pigmentation, this is preferably skin pigmentation. In other cases which are envisaged by the present invention, the type of pigmentation which must be modified concerns the pigmentation of the hair and nails, in particular the nails or body hair.

In accordance with a particularly preferred case of the present invention, the pigmentation the characteristics of which are to be modified is that of the hair system in general, and the hair of the head, moustache and eyebrows in particular. The present invention means that the phenomenon of halting the pigmentation of the hair, i.e. canities, can be modified, in particular when it occurs prematurely in an individual; this is known as premature canities.

For all therapeutic uses or methods, the active products used in the composition of a drug are preferably associated with pharmaceutically acceptable excipients. Any administration route which is considered to be acceptable may be used in the context of the invention, in particular an intradermal, intravenous, muscular, oral, otic, nasal, optical route. The formulation is preferably adapted to the selected administration route.

The uses for the manufacture of a drug of the invention may contain other active principles in their formulations. Similarly, administration of a drug as defined in the invention may be combined with administration of another drug, whether said administration is simultaneous, sequential or separate.

Similarly, the various polypeptides, molecules, agents or polynucleotide fragments as defined above which are used in the context of therapeutic uses may be combined and form part of the composition of a single drug, or may serve in the manufacture of various drugs. In particular, if they form part of the composition of distinct drugs, they may be administered at different frequencies, and/or at distinct times.

Particularly preferably, the therapeutic or cosmetic applications or methods envisaged in the context of the present invention concern the prevention or treatment of canities and particularly premature canities.

The present invention also concerns methods for the diagnosis of a predisposition to premature canities, preferably genetic premature canities (or hair graying). Premature canities is a phenotype which has been defined by the inventors as being characterized, inter alia, by the appearance of the first white hairs early in life, preferably towards 18 or 20 years of age.

Since this phenotype is transmitted to the next generation, it may prove to be important to individuals for whom a parent or close relative is affected to determine, before the appearance of symptoms, whether they will be affected or not. The diagnostic method of the invention is perfectly suited to individuals aged less than 18 years or even under 20 or 25 years.

Since it is very probable that environmental factors play a role in the "canities" phenotype and in that of "premature canities", the methods of the invention mean that the risks of development of such a phenotype, i.e. a predisposition to premature canities, can be evaluated.

In particular, the invention is directed towards a method for diagnosing a predisposition to premature canities in an individual, comprising the following steps:
 assay of a level of expression of the BNIPXL-beta transcript from a body sample derived from said individual; and
 comparison with a reference.

The body sample may be blood, a single drop being sufficient to carry out the method of the invention. Other body samples may be used in the context of the invention, such as the hair, body hair, urine or perspiration. The use of some cells from the individual may also be envisaged. The skilled person will be able to determine which sample could be used in the context of this test, while minimizing discomfort experienced by the individual undergoing it. Preferably, the body sample used in the diagnostic method described includes or is constituted by melanocyte cells.

The methods of the invention are not limited to the two steps described and may contain one or more steps anterior, posterior and/or intermediate to the steps mentioned.

The reference is preferably a value reflecting the level of expression of the BNIPXL-beta transcript in individuals who are manifestly free of a predisposition to premature canities. In contrast, it is clearly possible to define as the reference a level reflecting the degree of expression of the BNIPXL-beta transcript in individuals who are clearly affected by premature canities or predisposed to such a disorder.

KEY TO FIGURES

FIG. 1: clinical parameters for attributing a premature canities phenotype to tested individuals;

FIG. 1: illustrates the reference scale for the canities clinical index;

FIGS. 2 (2A and 2B): sequences relating to the BNIPXLβ protein;

FIG. 2A: illustrates the amino acid sequence for the protein BNIPXLβ, corresponding to SEQ ID NO: 1;

FIG. 2B illustrates the nucleotide sequence of the corresponding transcript (cDNA) corresponding to SEQ ID NO: 2; the strictly coding portion is identified in bold (coding from 163 to 2361).

EXPERIMENTAL SECTION

Meanings of Acronyms Used:
CNC: Conserved Non Coding region;
IVS: intervening sequence;
SNP: single nucleotide polymorphism.
Introduction In man, canities, or hair graying, is a common physical trait closely linked to ageing. In the European population, canities generally commences at about 45 to 55 years of age, starting on temporal areas of scalp.

Monogenic human syndromes have already been reported with a process of localized premature whitening/greying of the hair (or premature canities). Piebaldism, for example, which is a trait associated with Waardenburg's syndrome, is characterized by a premature whitening of the frontal area, and it has been linked with the genes PAX3 and MITF on chromosomes 3 and 2 respectively (Baldwin et al, 1994 and Tassabehji et al, 1994).

Further, it has frequently been observed that early whitening of the hair is hereditary in nature. Canities starts in childhood; it occurs before the age of 25 years and in some cases before the age of 18 years. Premature canities has been described as being associated with certain autoimmune disorders such as Biermer anemia or thyroiditis.

The present inventors have identified alleles linked to a risk of predisposition to premature canities (PC). Using linkage analyses and association analyses for samples of cohorts of selected families and controls, they have been able to identify a variability in the chromosomal region including the DDX31 and GTF3C4 genes on chromosome 9q. Further, using yeast two-hybrid analysis, the inventors have also been able to demonstrate the functional involvement of the protein DDX31 in the cascade responsible for pigmentation of the hair and nails and that of the protein BNIPXLβ.

Results
Determination of Phenotype

In this study, the "premature canities" phenotype (PC) was attributed only to those individuals (i) who presented with white hairs under 25 years of age and (ii) for whom half the hair of the head was gray at 30 years and who (iii) had familial antecedents of PC.

These characteristics were evaluated using a clinical scale in order to obtain, for each individual, a global phenotypic score (strong for scores of 5 and 4, moderate for scores 3 and 2, and weak for a score of 1; see FIG. 1 defining the premature canities index and Table 1).

TABLE 1

Method for attributing clinical score for premature canities.
For each individual, the three parameters were determined. The global phenotypic score was obtained by summing each of the parameters.

| Clinical parameters | | Score |
|---|---|---|
| Onset of whitening | Under 18 years | 2 |
| | Under 25 years | 1 |
| Significant whitening of all hair at 35 years | Canities index 3 | 2 |
| | Canities index 2 | 1 |
| Hereditary nature | Yes | 1 |
| | No | 0 |

Linkage Analysis for 12 Families:

For the linkage study carried out on the whole genome using microsatellite markers, 12 families were selected comprising 96 individuals (30 with PC, 55 without PC and 11 with uncertain phenotypes) based on power calculations starting from their pedigrees. This work has been described in particular in applications WO-04/007742 and FR-2 865 217.

On chromosome 9, the inventors determined a linkage interval at position 9q31-qter, between markers D9S290 and D9S158, with a maximum Lod score at position 151 cM on marker D9S158.

Association Study

An association study (affected/control) was carried out on the DNA from a group of individuals affected with PC (scores 3-5) and without a link between them, and a group of controls. This study identified 33 SNPs on chromosome 9 (SNPs rs2096071 to rs1378955) which showed a different allele frequency between individuals with PC and control individuals (Chi-2 test, $p<0.05$).

The next step was individual genotyping of positive SNPs on chromosome 9 the allele frequency of which differed substantially between those affected and the controls. The inventors then detected 4 SNPs with significant p values (see Table 2).

TABLE 2

SNPs of chromosome 9q34 showing a significant association with premature canities.

| Name of SNP | p value |
|---|---|
| rs306534 | $4.25 \times 10^{-3}$ |
| rs3739902 | $6 \times 10^{-5}$ |
| rs575916 | $3.5 \times 10^{-3}$ |
| rs365297 | $2 \times 10^{-3}$ |

Further, the haplotype "B86-92" (rs418320 and rs25260008) shows a significant association (p=0.0057) with the PC trait. This "B86-92" region was reduced with the addition of 35 supplemental SNPs. The SNP rs3739902, localized in intron 3 of the DDX31 gene (IVS3+268), proved the most significant ($p=6 \times 10^{-5}$).

The haplotype HAP86-88 was also particularly significant; it is defined by the SNPs: rs3739902, rs2583805 and rs377090. The statistical p-value of association of this haplotype with premature canities is less than $10^{-6}$.

A large block in linkage disequilibrium was observed by the inventors over the whole of the region comprising the positive SNPS. Two genes (DDX31, a member of the DEAD-box helicase protein family and GTF3C4, a potential transcription factor) were found in this block of linkage disequilibrium.

This work has been described in detail in applications WO04/007742 and FR2 865 217.

Sequence Analysis of Candidate Genes and Non-Coding Conserved Regions in the Region Within Haplotype HAP86-88.

The exons, the splicing sites, the 5' untranslated regions (5' UTR) and the conserved non coding regions in the region of haplotype HAP86-88 were sequenced for a selection of DNA from affected individuals. Six coding variants and four near-splice-site intronic variants were identified in individuals affected with premature canities (see Table 3).

TABLE 3

Variants identified during sequence analysis of genes DDX31 and GTF3C4, in 12 individuals affected with premature canities.

| Gene | Location | Exon/Intron | DNA variant | Functional significance |
|---|---|---|---|---|
| DDX31 | exon | 2 | c.413G > A | Synonymous |
| | intron | 3 | c.723 + 15G > C | Unknown significance |
| | intron | 4 | c.767 + 15_17delCTC | Unknown significance |
| | intron | 4 | c.767 + 55C > T | Synonymous, SNP rs4498679 |
| | intron | 11 | c.1176-16_13 delCTTA | Unknown significance |
| | exon | 13 | c.1674C > T | Synonymous, SNP rs306537 |

TABLE 3-continued

Variants identified during sequence analysis of genes DDX31 and GTF3C4, in 12 individuals affected with premature canities.

| Gene | Location | Exon/Intron | DNA variant | Functional significance |
|---|---|---|---|---|
| | exon | 20 | c.2398G > A | p.Ala800Thr |
| | exon | 20 | c.2395A > G | p.Ile799Val, SNP rs306547 |
| GTF3C4 | exon | 1 | c.36G > A | Synonymous |
| | exon | 3 | c.1560A > G | Synonymous |

The variant p.Ile799Val (c.2395A>G, also known as SNP rs306547), was found in 6 of the 12 DNA sequences from individuals with the heterozygous state and in 6 affected individuals, in the homozygotic state (p.V799). The $2^{nd}$ nonsense change p.Ala800Thr (c.2398G>A) was found in the heterozygotic state in one affected individual. In order to estimate the potential effect of this variant, the inventors analyzed a larger population of affected individuals (62) and controls (64). No other carrier of this mutation was found, either in the persons affected with PC or in the controls. Because the A800 residue was not conserved during the evolution of mammals, since the homologous residue in the mouse is threonine, like in the variant p.A800T, instead of alanine in the human gene, this event is highly probably silent from a biological viewpoint.

Another detected variant is the deletion of CTC in a CTC-CTC 2-unit repeated motif in intron 4 of the gene DDX31 (IVS4+15__17delCTC).

No variant was detected in the intergene sequence located in the two 5'UTR (untranslated regions) of the genes GTF3C4 and DDX31, which are orientated "head to head" with reference to the ATG codons.

The inventors identified 2 exonic variants in gene GTF3C4 (exons 2 and 3).

The inventors also analyzed 20 conserved non coding (CNC) sequences in this locus. Of them, just one variant was identified, transition c.2141-2018C>T, also known as SNP rs509762, located in intron 18 of the DDX31 gene (position 134479481, NCBI build126). A comparison of the genotypic and allelic frequencies showed that the PC genotype was over-represented in affected individuals with a score of 5 (45% in those with premature canities compared with 32% for the controls). This conserved non coding region, CNC, was conserved in the mouse, chicken and fugu.

Yeast Two-Hybrid

In order to further investigate the biological relevance of DDX31 as the gene for premature canities, and of GTF3C4, the inventors used the yeast "two-hybrid" technique in order to determine potential partners for interaction with isoforms such as transcripts of these genes.

Briefly, long form cDNA (full-length variant 1, amino acids 1-851) and short form cDNA (variant 2, truncated in C-terminal portion, amino acids 1-585) of DDX31 were amplified by the polymerase chain reaction from human melanocyte mRNA and were cloned into two types of vectors, i.e. pB27 (LexA, C-terminal fusion) and pB6 (Ga14, C-terminal fusion). Variant 2 of DDX31 codes for a 585 amino acid polypeptide which is truncated in the C-terminal region coded by exons 16 to 20 of variant 1.

These constructs were used as bait to screen a library of specific human melanocyte prey ($10^7$ independent clones). The single cDNA of GTF3C4 was also used as bait under the same conditions.

Cloning of the baits, construction of the library and establishing the interaction maps was consigned to Hybrigenics (Paris, France). The interactions were analyzed using PMRider® software using the procedures described by Rain J C et al, 2001.

For variants 1 and 2 of DDX31, respectively $1.90 \times 10^6$ and $38 \times 10^6$ interactions were tested with constructs pB27 and $45 \times 10^6$ and $119 \times 10^6$ interactions were tested with constructs pB6, respectively.

Of the 21 proteins potentially interacting with variant 1 of DDX31 and the 15 proteins potentially interacting with variant 2 of DDX31, PAX3 was identified as a protein which was susceptible of interacting with DDX31 with a predicted biological score in class "E" (PBS®, "predicted biological score", defined and determined by PMRider® software). This interaction was identified with the two forms, long and short, of DDX31. This interaction was centered on the DEAD "homeobox" domain of protein PAX3. It should be noted that it is known that mutations in the PAX3 protein are associated with type 1 Waardenburg syndrome.

A significant interaction was identified for GTF3C4 as well. Surprisingly and unexpectedly, the inventors also demonstrated that the protein BNIPXL-beta (Bcl2/adenovirus E1B 19 kDa protein-interacting protein 2) was a prey for the long form of DDX31 (variant 1). The confidence score as defined by the program was "C" (good confidence in interaction) with variant 1 of DDX31.

The results are shown in Table 4.

TABLE 4

| Protein name (bait) | Length of bait (AA) | Name of protein (prey) | Global biological score PIM ® (*) | Biological activity |
|---|---|---|---|---|
| DDX31 Long form (exons 1-20) NM_022779 | 1-852 | PAX3 | E | Transcription factor gene 3 domain paired Mutations associated with Waardenburg syndrome type 1 |
| DDX31 Short form (exons 1-15) NM_138620 | 1-585 | PAX3 | E | Transcription factor gene 3 domain paired Mutations associated with Waardenburg syndrome type 1 |

TABLE 4-continued

| Protein name (bait) | Length of bait (AA) | Name of protein (prey) | Global biological score PIM ® (*) | Biological activity |
|---|---|---|---|---|
| DDX31 Long form (exons 1-20) NM_022779 | 1-852 | BNIPXLβ | C | Protein interacting with Bcl2 and protein 19 kDa of adenovirus E1B. involved in suppression of cell death |

(*) See Rain et al, 2001.

Discussion

Premature canities represents a particularly informative clinical state in understanding the genetic bases of hair whitening, a trait which is generally associated with ageing.

Following an association study, the inventors have discovered a locus linked to PC on chromosome 9. Association analyses with SNPs has reduced the initial 10 Mbp linkage interval to a much smaller region of about 100 kbp. This region is organized into a single block in linkage disequilibrium which contains two genes: DDX31 and GTF3C4.

By assuming that premature canities could probably be a multigenic trait, and considering that the locus was obtained even though the number of affected individuals was limited, it could be concluded that most probably, this locus is susceptible of playing a major role in premature canities.

It should be noted that the results of the two-hybrid approach revealed that BNIPXLβ is a common prey of the long and short alternative isoforms of DDX31. BNIPXLβ is also a factor involved in the apoptosis process (Vegeto et al, 1999).

Sequencing of the coding, splicing and conserved non coding (CNC) sequences of the DNA from 12 individuals affected by PC with the most rigorous phenotypes has allowed several variants to be identified. In DDX31, the variant p.Ala800Thr in exon 20, not recorded as a polymorphism, could be at the origin of a functional effect linked to premature canities. The variation IVS4+15__17delCTC is located in a non conserved region in mammals and it was not predicted that this region could alter the splicing of intron 4 (splice view analysis). This variant could be associated with the genetic variation responsible for the phenotypic trait.

The variation within CNChs8, in intron 18 of the DDX31 gene, has a better phenotypic potential because it is located in a portion of sequences which have proved highly conserved in the mouse (no gap, no change over a distance of 100 base pairs). Interestingly, the two-hybrid approach has demonstrated that DDX31 and GTF3C4, both located in the region involved in premature canities, have a common interaction with PAX3, a protein which has long been suspected of participating in the pigmentation process.

It should also be noted that DDX31 codes for a helicase. In Werner's syndrome, corresponding to accelerated ageing in which premature whitening of the hair is observed, it has been reported that the gene which is responsible codes for a helicase (WRN) (Yu et al, 1996). Surprisingly and unexpectedly, the inventors have discovered that BNIPXL (BCl2/adenovirus E1B 19 kDa protein-interacting protein 2) is a prey of DDX31. The confidence score in the interaction is particularly good.

The interaction between DDX31 and BNIPXL-beta is thus probably important in vesicular traffic, hence a role in migration and transfer of melanosomes and thus canities and premature canities.

Material and Methods

Affected Individuals, Linkage Study and Association Study

The choice of individuals and their classification was made as indicated in applications FR-2 842 104, FR-2 853 532, FR-2 865 217 and WO-04/007742.

The linkage and association studies were also described in those patent applications as well as in the abstracts by Blouin et al, 2006 and Lacharrière et al, 2007.

To recapitulate, in a first step, the inventors genotyped samples collecting the DNA from affected individuals compared with paired controls for a selection of SNPa included in the interval of chromosome 9 showing a significant linkage with the premature canities trait.

The region corresponding to the linkage interval on chromosome 9q34 was defined between the SNP markers rs2096071 and rs1099298 (between positions 123'405'258 bp and 132'547'291 bp, expressed as a function of the 2001 version (i.e. NCBI Build28); between positions 130'565'549 and 139'556'369 in version 37; genome.cse.uscsc.edu).

A given SNP is deemed to be "positive" if it has a significant deviation in the allele frequency. Each region which satisfies at least one of the following conditions: (i) at least 2 contiguous positive SNPs and (ii) 2 positive SNPs separated by a single negative SNP; was selected for the individual genotyping phase.

In order to test the association of the selected SNPs with the PC phenotype in each individually genotyped DNA (phase 2 of the analysis), the inventors compared the allelic frequency or the genotypic frequency of each SNP in affected and control populations.

In order to capture all of the genetic variation in this region, the inventors also performed haplotype analysis using a sliding window of the SNPs (comprising 5 SNPs each time, with an increment of 1) in order to efficiently reconstruct the haplotype.

Sequencing

DNA from individuals with PC was amplified for the exons of the genes GTF3C4 and DDX31, the small intergene region between these genes and at the regions comprising the CNC sequences with at least 70% identity between human and mouse (no gap), and sequenced using conventional methods.

Two-Hybrid

Cloning of baits, construction of the library and interaction map establishment was carried out by Hybrigenics (Paris, France). Interaction analysis was carried out using PMRider® software in accordance with the procedures described by Rain et al, 2001. The long and short splice variants of DDX31 (GenBank accession numbers NM__022779 and NM__138620 respectively), the human protein STX17 (GenBank accession number NM__017919) were cloned into pB27 in phase with LexA and into pB6 in phase with the DNA binding domain of Gal4. The four constructs were used as bait to screen a library of specific human melanocyte cDNA, constructed in pP6. Plasmids pB27, pB6 and pP6 were derived from plasmids pBTM116 (Vojtek and Hollenberg, 1995), pAS2ΔΔ (Fromont-Racine et al., 1997) and pGADGH (Bartel et al, 1993), respectively.

An average of 73 million clones (7 times the complexity of the library) were screened for each bait, using a mating approach with yeast strains L40-Gal4 (mat a) and Y187 (mat a) as described by Fromont-Racine et al., 1997. His+ colonies were selected on a medium free of tryptophan, leucine and histidine. The fragments of prey from positive clones were amplified by PCR and sequenced at their 3' and 5' junctions on a PE3700 sequencer. The resulting sequences were used to identify the corresponding proteins interacting in the GenBank database (NCBI) using a completely automated process. A confidence score was attributed to each interaction in the manner described above (Formstecher et al, 2005).

The local score is the probability for a given interacting domain ("Selected interacting domain", SID®) of being obtained assuming an equal chance hypothesis, i.e. as a result of random noise. It may be deduced by combining the probabilities p (using a binomial law) of each of the independent fragments defining it. A (global) predicted biological score (PBS) is calculated for each of the interaction proteins after collecting the results of each screening. By assuming that the events are independent, the scores of the various screenings are combined together when the same pair of protein domains is concerned. The resulting PBS thus represents the probability that a given protein-protein interaction will be due to noise.

The scores are real numbers in the range 0 to 1, but in practice they are collected into four categories (classes A, B, C and D). Finally, the overall connectivity of the interaction map is analyzed in order to separately label (category E) the selected interaction domains (SID) found as prey at a higher frequency at a fixed threshold: the PBS of each protein-protein interaction involving very strongly linked SIDs is set to 1. At the same time the thresholds between the categories and the strong bonding threshold are defined manually taking into account the nature of the organism under study, the library used and the present proteome coverage ($A<1^e610<B<1^e-5<C<1^e-2,5<D$; category E corresponds to prey SIDs selected with more than 4 baits and has been arbitrarily attributed the value 1.

In view of the above, the present invention more specifically concerns the following points:

A polypeptide comprising a sequence having at least 90% identity with all or part of the sequence SEQ ID NO: 1, for therapeutic use in the treatment or prevention of premature canities in humans, said portion comprising at least 30 amino acids.

A molecule comprising a RNAi sequence having at least 90% identity with all or part of the sequence SEQ ID NO: 2 for therapeutic use in the treatment or prevention of premature canities in humans, said portion comprising at least 18 nucleotides.

A method (A) for screening molecules modulating the expression of a gene coding for BNIPXL-beta in order to identify an agent for use for cosmetic or therapeutic purposes, in the field of pigmentation.

Said method (A) may comprise the following steps:
bringing a test molecule into the presence of a gene coding for BNIPXL-beta under conditions allowing expression of said gene in the absence of the test molecule; and
detecting a variation in the level of expression of said gene due to the presence of the test molecule.

In said method (A), the modulation of expression may be inhibition of transcription or translation of a gene coding for BNIPXL-beta.

In said method (A), the test molecules may be proteins, RNAi's, ribozymes or antisense RNA targeting the gene coding for BNIPXL-beta.

A method (B) for screening molecules modulating the activity of the polypeptide BNIPXL-beta, to identify an agent for use for cosmetic or therapeutic purposes, in the field of pigmentation.

The screening method (B) may comprise the following steps:
bringing the test molecule into the presence of the polypeptide BNIPXL-beta, under conditions allowing the activity of said polypeptide in the absence of the test molecule to be determined; and
detecting a variation in the activity of said polypeptide due to the presence of the test molecule.

In said screening method (B), the modulation of activity may be total or partial inhibition, In said screening method (B), the modulation of the activity may be carried out by sequestration of said polypeptide, In said screening method (B), the test molecules may be antibodies directed against the polypeptide BNIPXL-beta or a portion thereof, In said screening method (B), the pigmentation may be that of the hair and nails, preferably the hair.

Use of an agent modulating the expression of the gene coding for BNIPXL-beta, for cosmetic purposes in the field of pigmentation.

Use of an agent modulating the expression of the gene coding for BNIPXL-beta, for the manufacture of a drug for a therapeutic use in the field of pigmentation.

Use of an agent modulating the activity of a polypeptide derived from translation of a gene coding for BNIPXL-beta, for cosmetic purposes in the field of pigmentation.

Use of an agent modulating the activity of a polypeptide derived from translation of the gene coding for BNIPXL-beta, for the production of a drug for therapeutic use in the field of pigmentation.

Use of at least one polynucleotide fragment comprising at least 18 consecutive nucleotides the sequence of which corresponds to all or part of the gene coding for BNIPXL-beta or a BNIPXL-beta transcript, for cosmetic purposes, in the field of pigmentation.

The previous uses preferably concern the prevention or treatment of canities, more specifically premature canities.

A method (C) for diagnosing a predisposition to premature canities in an individual, comprising the following steps:
i) assay of a level of expression of a BNIPXL-beta transcript using a body sample from said individual;
ii) comparison with a reference level.

In said diagnosis method (C), the reference level may be the level of expression of a BNIPXL-beta transcript in an unaffected individual.

In said diagnosis method (C), the body sample may comprise or may be constituted by melanocyte cells.

A method (D) for screening molecules modulating the interaction between a BNIPXL-beta polypeptide and a polypeptide derived from translation of the DDX31 gene, to identify an agent for use for cosmetic or therapeutic purposes in the field of pigmentation.

In said screening method (D), the modulation may be a disruption of the association between the two polypeptides or a modification of the association constant between the two polypeptides.

In said screening method (D), the identified agent may be a competitive inhibitor of the association between the two polypeptides.

In said screening method (D), the pigmentation may be that of the hair and nails, preferably the hair.

Use of an agent modulating the interaction between BNIPXL-beta and a polypeptide derived from translation of the gene DDX31, for cosmetic purposes, in the field of pigmentation.

Use of an agent modulating the interaction between BNIPXL-beta and a polypeptide derived from translation of the gene DDX31, for the manufacture of a drug for therapeutic use in the field of pigmentation.

In said uses, the agent may be an antibody.

REFERENCES

Belcredito, S., et al. 2001. Estrogen neuroprotection: the involvement of the Bcl-2 binding protein BNIP2. *Brain Res Brain Res Rev* 37: 335-342.

Blouin, J L et al. Localisation of a gene for Human Premature Hair Greying on chromosome 9q34. Congress of the American Society of Human Genetics, Oct. 2006.

Commo, S. & Bernard, B. A. 2000. Melanocyte subpopulation turnover during the human hair cycle: an immunohistochemical study. Pigment Cell Res. 13:253-259

Commo S., Gaillard O., Thibaut S.,& Bernard B. A. 2004. Absence of TRP-2 in melanogenic melanocytes of human hair. *Pigment Cell Res.* 17:488-497

Commo, S., Gaillard, O. & Bernard, B. A. Human hair greying is linked to a specific depletion of hair follicle melanocytes affecting both the bulb and the outer root sheath. *Br J Dermatol* 150, 435-43 (2004).

Formstecher, E. et al. Protein interaction mapping: a Drosophila case study. *Genome Res* 15, 376-84 (2005).

Fromont-Racine, M., Rain, J. C. & Legrain, P. Towards a functional analysis of the yeast genome through exhaustive two-hybrid screens. *Nat Genet* 16, 277-82 (1997).

de Lacharrière O., et al. A gene for premature hair greying maps to chromosome 9q34. World Congress of Dermatology, October 2007.

Machida, T., et al. 2006. Increased expression of proapoptotic BMCC1, a novel gene with the BNIP2 and Cdc42GAP homology (BCH) domain, is associated with favorable prognosis in human neuroblastomas. *Oncogene* 25: 1931-1942.

Mousley, C. J., et al. 2007. The Sec14-superfamily and the regulatory interface between phospholipid metabolism and membrane trafficking. *Biochim Biophys Acta* 1771: 727-736.

Qin, W., et al. 2003. BNIPL-2, a novel homologue of BNIP-2, interacts with Bcl-2 and Cdc42GAP in apoptosis. *Biochem Biophys Res Commun* 308: 379-385.

Rain, J. C. et al. The protein-protein interaction map of Helicobacter pylori. *Nature* 409, 211-5 (2001).

Shang, X., et al. 2003. Concerted regulation of cell dynamics by BNIP-2 and Cdc42GAP homology/Sec14p-like, proline-rich, and GTPase-activating protein domains of a novel Rho GTPase-activating protein, BPGAP1. *J Biol Chem* 278: 45903-45914.

Sirokmany, G., et al. 2006. Sec14 homology domain targets p50RhoGAP to endosomes and provides a link between Rab and Rho GTPases. *J Biol Chem* 281: 6096-6105.

Tassabehji, M., Newton, V. E. & Read, A. P. Waardenburg syndrome type 2 caused by mutations in the human microphthalmia (MITF) gene. *Nat Genet* 8, 251-5 (1994).

Vegeto, E., et al Estrogen and progesterone induction of survival of monoblastoid cells undergoing TNF-alpha-induced apoptosis. *Faseb J* 13, 793-803 (1999).

Vojtek, A. B. & Hollenberg, S. M. Ras-Raf interaction: two-hybrid analysis. *Methods Enzymol* 255, 331-42 (1995).

Yu, C. E. et al. Positional cloning of the Werner's syndrome gene. *Science* 272, 258-62 (1996).

Zhou, Y. T., Guy, G. R. & Low, B. C. 2005. BNIP-2 induces cell elongation and membrane protrusions by interacting with Cdc42 via a unique Cdc42-binding motif within its BNIP-2 and Cdc42GAP homology domain. *Exp Cell Res* 303: 263-274.

The invention claimed is:

1. A method for diagnosing a predisposition to premature canities in an individual comprising the following steps:
   i) measuring the level of expression of a BNIPXL-beta transcript in a sample comprising melanocyte cells from said individual; and
   ii) comparing the level measured in step i) with a reference level of expression of a BNIPXL-beta transcript in a sample comprising melanocyte cells from an individual unaffected by premature canities;
   wherein a higher level of expression of BNIPXL-beta transcript determined in step i) as compared to the reference level indicates the individual is predisposed to premature canities.

2. The method according to claim 1, wherein the individual to be diagnosed is less than 25 years of age.

3. The method according to claim 1, wherein the individual to be diagnosed is less than 20 years of age.

4. The method according to claim 1, wherein the individual to be diagnosed is less than 18 years of age.

* * * * *

SEQUENCE LISTING

```
<160> NUMBER OF SEQ ID NOS: 3

<210> SEQ ID NO 1
<211> LENGTH: 732
<212> TYPE: PRT
<213> ORGANISM: Homo sapiens

<400> SEQUENCE: 1

Met Ser Lys Leu Thr Leu Ser Glu Gly His Pro Glu Thr Pro Val Asp
1               5                   10                  15

Gly Asp Leu Gly Lys Gln Asp Ile Cys Ser Ser Glu Ala Ser Trp Gly
            20                  25                  30

Asp Phe Glu Tyr Asp Val Met Gly Gln Asn Ile Asp Glu Asp Leu Leu
        35                  40                  45

Arg Glu Pro Glu His Phe Leu Tyr Gly Gly Asp Pro Pro Leu Glu Glu
    50                  55                  60

Asp Ser Leu Lys Gln Ser Leu Ala Pro Tyr Thr Pro Pro Phe Asp Leu
65                  70                  75                  80

Ser Tyr Ile Thr Glu Pro Ala Gln Ser Ala Glu Thr Ile Glu Glu Ala
                85                  90                  95

Gly Ser Pro Glu Asp Glu Ser Leu Gly Cys Arg Ala Ala Glu Ile Val
            100                 105                 110
```

-continued

Leu Ser Ala Leu Pro Asp Arg Arg Ser Glu Gly Asn Gln Ala Glu Thr
        115                 120                 125
Lys Asn Arg Leu Pro Gly Ser Gln Leu Ala Val Leu His Ile Arg Glu
        130                 135                 140
Asp Pro Glu Ser Val Tyr Leu Pro Val Gly Ala Gly Ser Asn Ile Leu
145                 150                 155                 160
Ser Pro Ser Asn Val Asp Trp Glu Val Glu Thr Asp Asn Ser Asp Leu
                165                 170                 175
Pro Ala Gly Gly Asp Ile Gly Pro Asn Gly Ala Ser Lys Glu Ile
            180                 185                 190
Ser Glu Leu Glu Glu Lys Thr Ile Pro Thr Lys Glu Pro Glu Gln
        195                 200                 205
Ile Lys Ser Glu Tyr Lys Glu Arg Cys Thr Glu Lys Asn Glu Asp
        210                 215                 220
Arg His Ala Leu His Met Asp Tyr Ile Leu Val Asn Arg Glu Glu Asn
225                 230                 235                 240
Ser His Ser Lys Pro Glu Thr Cys Glu Glu Arg Glu Ser Ile Ala Glu
                245                 250                 255
Leu Glu Leu Tyr Val Gly Ser Lys Glu Thr Gly Leu Gln Gly Thr Gln
            260                 265                 270
Leu Ala Ser Phe Pro Asp Thr Cys Gln Pro Ala Ser Leu Asn Glu Arg
        275                 280                 285
Lys Gly Leu Ser Ala Glu Lys Met Ser Ser Lys Ser Asp Thr Arg Ser
        290                 295                 300
Ser Phe Glu Ser Pro Ala Gln Asp Gln Ser Trp Met Phe Leu Gly His
305                 310                 315                 320
Ser Glu Val Gly Asp Pro Ser Leu Asp Ala Arg Asp Ser Gly Pro Gly
                325                 330                 335
Trp Ser Gly Lys Thr Val Glu Pro Phe Ser Glu Leu Gly Leu Gly Glu
            340                 345                 350
Gly Pro Gln Leu Gln Ile Leu Glu Glu Met Lys Pro Leu Glu Ser Leu
        355                 360                 365
Ala Leu Glu Glu Ala Ser Gly Pro Val Ser Gln Ser Gln Lys Ser Lys
        370                 375                 380
Ser Arg Gly Arg Ala Gly Pro Asp Ala Val Thr His Asp Asn Glu Trp
385                 390                 395                 400
Glu Met Leu Ser Pro Gln Pro Val Gln Lys Asn Met Ile Pro Asp Thr
                405                 410                 415
Glu Met Glu Glu Glu Thr Glu Phe Leu Glu Leu Gly Thr Arg Ile Ser
            420                 425                 430
Arg Pro Asn Gly Leu Leu Ser Glu Asp Val Gly Met Asp Ile Pro Phe
        435                 440                 445
Glu Glu Gly Val Leu Ser Pro Ser Ala Ala Asp Met Arg Pro Glu Pro
        450                 455                 460
Pro Asn Ser Leu Asp Leu Asn Asp Thr His Pro Arg Arg Ile Lys Leu
465                 470                 475                 480
Thr Ala Pro Asn Ile Asn Leu Ser Leu Asp Gln Ser Glu Gly Ser Ile
                485                 490                 495
Leu Ser Asp Asp Asn Leu Asp Ser Pro Asp Glu Ile Asp Ile Asn Val
            500                 505                 510
Asp Glu Leu Asp Thr Pro Asp Glu Ala Asp Ser Phe Glu Tyr Thr Gly
        515                 520                 525
His Glu Asp Pro Thr Ala Thr Lys Asp Ser Gly Gln Glu Ser Glu Ser
530                 535                 540

```
Ile Pro Glu Tyr Thr Ala Glu Glu Arg Glu Asp Asn Arg Leu Trp
545                 550                 555                 560

Arg Thr Val Val Ile Gly Asp Gln Gln Arg Ile Asp Met Lys Val
            565                 570                 575

Ile Glu Pro Tyr Arg Arg Val Ile Ser His Gly Gly Leu Arg Gly Tyr
                580                 585                 590

Tyr Gly Asp Gly Leu Asn Ala Ile Val Phe Ala Ala Cys Phe Leu
        595                 600                 605

Pro Asp Ser Ser Arg Ala Asp Tyr His Tyr Val Met Glu Asn Leu Phe
        610                 615                 620

Leu Tyr Val Ile Ser Thr Leu Glu Leu Met Val Ala Glu Asp Tyr Met
625                 630                 635                 640

Ile Val Tyr Leu Asn Gly Ala Thr Pro Arg Arg Met Pro Gly Leu
                645                 650                 655

Gly Trp Met Lys Lys Cys Tyr Gln Met Ile Asp Arg Arg Leu Arg Lys
        660                 665                 670

Asn Leu Lys Ser Phe Ile Ile Val His Pro Ser Trp Phe Ile Arg Thr
            675                 680                 685

Ile Leu Ala Val Thr Arg Pro Phe Ile Ser Ser Lys Phe Ser Ser Lys
690                 695                 700

Ile Lys Tyr Val Asn Ser Leu Ser Glu Leu Ser Gly Leu Ile Pro Met
705                 710                 715                 720

Asp Cys Ile His Ile Pro Glu Ser Ile Ile Lys Tyr
                725                 730

<210> SEQ ID NO 2
<211> LENGTH: 2405
<212> TYPE: DNA
<213> ORGANISM: Homo sapiens
<220> FEATURE:
<221> NAME/KEY: CDS
<222> LOCATION: (163)..(2361)

<400> SEQUENCE: 2
gctttgtttg atggtgatcc acatttatcc acagagaatc ctgccttggt tcctgatgct      60
ttgctagcct cagacacttg tctggatata agcgaagctg cctttgacca cagtttcagc     120
gatgcctcag gtctcaacac atccacggga acaatagatg ac atg agt aaa ctg         174
                                              Met Ser Lys Leu
                                                1 aca tta tcc gaa ggc cat ccg gaa acg cca gtt gat ggg gac cta ggg       222
Thr Leu Ser Glu Gly His Pro Glu Thr Pro Val Asp Gly Asp Leu Gly
5                   10                  15                  20 aag caa gat atc tgc tca tct gaa gcc tcg tgg ggt gat ttt gaa tat       270
Lys Gln Asp Ile Cys Ser Ser Glu Ala Ser Trp Gly Asp Phe Glu Tyr
                25                  30                  35 gat gta atg ggc cag aat atc gat gaa gat tta ctg aga gag cct gaa       318
Asp Val Met Gly Gln Asn Ile Asp Glu Asp Leu Leu Arg Glu Pro Glu
            40                  45                  50 cac ttc ctg tat ggt ggt gac cct cct ttg gag gaa gat tct ctg aag       366
His Phe Leu Tyr Gly Gly Asp Pro Pro Leu Glu Glu Asp Ser Leu Lys
        55                  60                  65 cag tcg ctg gca ccg tac aca cct ccc ttt gat ttg tct tat atc aca       414
Gln Ser Leu Ala Pro Tyr Thr Pro Pro Phe Asp Leu Ser Tyr Ile Thr
    70                  75                  80 gaa cct gcc cag agt gct gaa aca ata gag gaa gct ggg tct cca gag       462
Glu Pro Ala Gln Ser Ala Glu Thr Ile Glu Glu Ala Gly Ser Pro Glu
85                  90                  95                  100
```

-continued

| | |
|---|---|
| gat gaa tct ctg gga tgc aga gca gca gag ata gtg ctt tct gca ctt<br>Asp Glu Ser Leu Gly Cys Arg Ala Ala Glu Ile Val Leu Ser Ala Leu<br>105                      110                      115 | 510 |
| cct gat cga aga agt gag gga aac cag gct gag acc aaa aac aga ctg<br>Pro Asp Arg Arg Ser Glu Gly Asn Gln Ala Glu Thr Lys Asn Arg Leu<br>120                      125                      130 | 558 |
| cct gga tcc cag ctg gct gtg ctg cat att cgt gaa gac cct gag tcc<br>Pro Gly Ser Gln Leu Ala Val Leu His Ile Arg Glu Asp Pro Glu Ser<br>135                      140                      145 | 606 |
| gtt tat ttg ccg gta gga gca ggc tcc aac att ttg tct cca tca aac<br>Val Tyr Leu Pro Val Gly Ala Gly Ser Asn Ile Leu Ser Pro Ser Asn<br>150                      155                      160 | 654 |
| gtt gac tgg gaa gta gaa aca gat aat tct gat tta cca gca ggt gga<br>Val Asp Trp Glu Val Glu Thr Asp Asn Ser Asp Leu Pro Ala Gly Gly<br>165                      170                      175                      180 | 702 |
| gac ata gga cca cca aat ggt gcc agc aag gaa ata tca gaa ttg gaa<br>Asp Ile Gly Pro Pro Asn Gly Ala Ser Lys Glu Ile Ser Glu Leu Glu<br>                     185                      190                      195 | 750 |
| gaa gaa aaa aca att cct acc aaa gag cct gag cag ata aaa tca gaa<br>Glu Glu Lys Thr Ile Pro Thr Lys Glu Pro Glu Gln Ile Lys Ser Glu<br>                     200                      205                      210 | 798 |
| tac aag gaa gaa aga tgt aca gag aag aat gaa gat cgt cat gca cta<br>Tyr Lys Glu Glu Arg Cys Thr Glu Lys Asn Glu Asp Arg His Ala Leu<br>                     215                      220                      225 | 846 |
| cac atg gat tac ata ctt gta aac cgt gaa gaa aat tca cac tca aag<br>His Met Asp Tyr Ile Leu Val Asn Arg Glu Glu Asn Ser His Ser Lys<br>230                      235                      240 | 894 |
| cca gag acc tgt gaa gaa aga gaa agc ata gct gaa tta gaa ttg tat<br>Pro Glu Thr Cys Glu Glu Arg Glu Ser Ile Ala Glu Leu Glu Leu Tyr<br>245                      250                      255                      260 | 942 |
| gta ggt tcc aaa gaa aca ggg ctg cag gga act cag tta gca agc ttc<br>Val Gly Ser Lys Glu Thr Gly Leu Gln Gly Thr Gln Leu Ala Ser Phe<br>                     265                      270                      275 | 990 |
| cca gac aca tgt cag cca gcc tcc tta aat gaa aga aaa ggt ctc tct<br>Pro Asp Thr Cys Gln Pro Ala Ser Leu Asn Glu Arg Lys Gly Leu Ser<br>                     280                      285                      290 | 1038 |
| gca gag aaa atg tct tct aaa agc gat acg aga tca tct ttt gaa agc<br>Ala Glu Lys Met Ser Ser Lys Ser Asp Thr Arg Ser Ser Phe Glu Ser<br>295                      300                      305 | 1086 |
| cct gca caa gac cag agt tgg atg ttc ttg ggc cat agt gag gtt ggt<br>Pro Ala Gln Asp Gln Ser Trp Met Phe Leu Gly His Ser Glu Val Gly<br>310                      315                      320 | 1134 |
| gat cca tca ctg gat gcc agg gac tca ggg cct ggg tgg tcc ggc aag<br>Asp Pro Ser Leu Asp Ala Arg Asp Ser Gly Pro Gly Trp Ser Gly Lys<br>325                      330                      335                      340 | 1182 |
| act gtg gag ccg ttc tct gaa ctc ggc ttg ggt gag ggt ccc cag ctg<br>Thr Val Glu Pro Phe Ser Glu Leu Gly Leu Gly Glu Gly Pro Gln Leu<br>                     345                      350                      355 | 1230 |
| cag att ctg gaa gaa atg aag cct cta gaa tct tta gca cta gag gaa<br>Gln Ile Leu Glu Glu Met Lys Pro Leu Glu Ser Leu Ala Leu Glu Glu<br>                     360                      365                      370 | 1278 |
| gcc tct ggt cca gtc agc caa tca cag aag agt aag agc cga ggc agg<br>Ala Ser Gly Pro Val Ser Gln Ser Gln Lys Ser Lys Ser Arg Gly Arg<br>                     375                      380                      385 | 1326 |
| gct ggc ccg gat gca gtt acc cat gac aat gaa tgg gaa atg ctt tca<br>Ala Gly Pro Asp Ala Val Thr His Asp Asn Glu Trp Glu Met Leu Ser<br>390                      395                      400 | 1374 |
| cca cag cct gtt cag aaa aac atg atc cct gac acg gaa atg gag gag<br>Pro Gln Pro Val Gln Lys Asn Met Ile Pro Asp Thr Glu Met Glu Glu<br>405                      410                      415                      420 | 1422 |

```
gag aca gag ttc ctt gag ctc gga acc agg ata tca aga cca aat gga      1470
Glu Thr Glu Phe Leu Glu Leu Gly Thr Arg Ile Ser Arg Pro Asn Gly
            425                 430                 435 cta ctg tca gag gat gta gga atg gac atc ccc ttt gaa gag ggc gtg      1518
Leu Leu Ser Glu Asp Val Gly Met Asp Ile Pro Phe Glu Glu Gly Val
            440                 445                 450 ctg agt ccc agt gct gca gac atg agg cct gaa cct cct aat tct ctg      1566
Leu Ser Pro Ser Ala Ala Asp Met Arg Pro Glu Pro Pro Asn Ser Leu
            455                 460                 465 gat ctt aat gac act cat cct cgg aga atc aag ctc aca gcc cca aat      1614
Asp Leu Asn Asp Thr His Pro Arg Arg Ile Lys Leu Thr Ala Pro Asn
            470                 475                 480 atc aat ctt tct ctg gac caa agt gaa gga tct att ctc tct gat gat      1662
Ile Asn Leu Ser Leu Asp Gln Ser Glu Gly Ser Ile Leu Ser Asp Asp
485                 490                 495                 500 aac ttg gac agc cca gat gaa att gac atc aat gtg gat gaa ctt gat      1710
Asn Leu Asp Ser Pro Asp Glu Ile Asp Ile Asn Val Asp Glu Leu Asp
                505                 510                 515 acc ccc gat gaa gca gat tct ttt gag tac act ggc cat gaa gat ccc      1758
Thr Pro Asp Glu Ala Asp Ser Phe Glu Tyr Thr Gly His Glu Asp Pro
            520                 525                 530 aca gcc acc aaa gat tct ggc caa gag tca gag tct att cca gaa tat      1806
Thr Ala Thr Lys Asp Ser Gly Gln Glu Ser Glu Ser Ile Pro Glu Tyr
            535                 540                 545 acg gcc gaa gag gaa cgg gag gac aac cgg ctt tgg agg aca gtg gtc      1854
Thr Ala Glu Glu Glu Arg Glu Asp Asn Arg Leu Trp Arg Thr Val Val
            550                 555                 560 att gga gac caa gag cag cgc att gac atg aag gtc atc gag ccc tac      1902
Ile Gly Asp Gln Glu Gln Arg Ile Asp Met Lys Val Ile Glu Pro Tyr
565                 570                 575                 580 agg aga gtc att tct cac gga gga ctt aga gga tac tat ggg gac ggt      1950
Arg Arg Val Ile Ser His Gly Gly Leu Arg Gly Tyr Tyr Gly Asp Gly
                585                 590                 595 cta aat gcc atc att gtg ttt gcc gcc tgt ttt ctg cca gac agc agt      1998
Leu Asn Ala Ile Ile Val Phe Ala Ala Cys Phe Leu Pro Asp Ser Ser
            600                 605                 610 cgg gcg gat tac cac tat gtc atg gaa aat ctt ttc cta tat gta ata      2046
Arg Ala Asp Tyr His Tyr Val Met Glu Asn Leu Phe Leu Tyr Val Ile
            615                 620                 625 agt act tta gag ttg atg gta gct gaa gac tat atg att gtg tac ttg      2094
Ser Thr Leu Glu Leu Met Val Ala Glu Asp Tyr Met Ile Val Tyr Leu
            630                 635                 640 aat ggt gca acc cca aga agg agg atg cca ggg cta ggc tgg atg aag      2142
Asn Gly Ala Thr Pro Arg Arg Arg Met Pro Gly Leu Gly Trp Met Lys
645                 650                 655                 660 aaa tgc tac cag atg att gac aga cgg ttg agg aag aat ttg aaa tca      2190
Lys Cys Tyr Gln Met Ile Asp Arg Arg Leu Arg Lys Asn Leu Lys Ser
                665                 670                 675 ttc atc att gtt cat cca tct tgg ttc atc aga aca atc ctt gct gtg      2238
Phe Ile Ile Val His Pro Ser Trp Phe Ile Arg Thr Ile Leu Ala Val
            680                 685                 690 aca cga cct ttt ata agt tca aaa ttc agc agt aaa att aaa tat gtc      2286
Thr Arg Pro Phe Ile Ser Ser Lys Phe Ser Ser Lys Ile Lys Tyr Val
            695                 700                 705 aat agc tta tca gaa ctc agt ggg ctg atc cca atg gat tgc atc cac      2334
Asn Ser Leu Ser Glu Leu Ser Gly Leu Ile Pro Met Asp Cys Ile His
710                 715                 720 att cca gag agc atc atc aaa tat tga cttgaagctg aaagaaaagc            2381
Ile Pro Glu Ser Ile Ile Lys Tyr
725                 730
```
cttagttggc catgctggaa gaag    2405

<210> SEQ ID NO 3
<211> LENGTH: 732
<212> TYPE: PRT
<213> ORGANISM: Homo sapiens

<400> SEQUENCE: 3

```
Met Ser Lys Leu Thr Leu Ser Glu Gly His Pro Glu Thr Pro Val Asp
1               5                   10                  15

Gly Asp Leu Gly Lys Gln Asp Ile Cys Ser Ser Glu Ala Ser Trp Gly
            20                  25                  30

Asp Phe Glu Tyr Asp Val Met Gly Gln Asn Ile Asp Glu Asp Leu Leu
        35                  40                  45

Arg Glu Pro Glu His Phe Leu Tyr Gly Asp Pro Pro Leu Glu Glu
    50                  55                  60

Asp Ser Leu Lys Gln Ser Leu Ala Pro Tyr Thr Pro Pro Phe Asp Leu
65                  70                  75                  80

Ser Tyr Ile Thr Glu Pro Ala Gln Ser Ala Glu Thr Ile Glu Glu Ala
                85                  90                  95

Gly Ser Pro Glu Asp Glu Ser Leu Gly Cys Arg Ala Ala Glu Ile Val
            100                 105                 110

Leu Ser Ala Leu Pro Asp Arg Arg Ser Glu Gly Asn Gln Ala Glu Thr
        115                 120                 125

Lys Asn Arg Leu Pro Gly Ser Gln Leu Ala Val Leu His Ile Arg Glu
    130                 135                 140

Asp Pro Glu Ser Val Tyr Leu Pro Val Gly Ala Gly Ser Asn Ile Leu
145                 150                 155                 160

Ser Pro Ser Asn Val Asp Trp Glu Val Glu Thr Asp Asn Ser Asp Leu
                165                 170                 175

Pro Ala Gly Gly Asp Ile Gly Pro Pro Asn Gly Ala Ser Lys Glu Ile
            180                 185                 190

Ser Glu Leu Glu Glu Glu Lys Thr Ile Pro Thr Lys Glu Pro Glu Gln
        195                 200                 205

Ile Lys Ser Glu Tyr Lys Glu Glu Arg Cys Thr Glu Lys Asn Glu Asp
    210                 215                 220

Arg His Ala Leu His Met Asp Tyr Ile Leu Val Asn Arg Glu Glu Asn
225                 230                 235                 240

Ser His Ser Lys Pro Glu Thr Cys Glu Glu Arg Glu Ser Ile Ala Glu
                245                 250                 255

Leu Glu Leu Tyr Val Gly Ser Lys Glu Thr Gly Leu Gln Gly Thr Gln
            260                 265                 270

Leu Ala Ser Phe Pro Asp Thr Cys Gln Pro Ala Ser Leu Asn Glu Arg
        275                 280                 285

Lys Gly Leu Ser Ala Glu Lys Met Ser Ser Lys Ser Asp Thr Arg Ser
    290                 295                 300

Ser Phe Glu Ser Pro Ala Gln Asp Gln Ser Trp Met Phe Leu Gly His
305                 310                 315                 320

Ser Glu Val Gly Asp Pro Ser Leu Asp Ala Arg Asp Ser Gly Pro Gly
                325                 330                 335

Trp Ser Gly Lys Thr Val Glu Pro Phe Ser Glu Leu Gly Leu Gly Glu
            340                 345                 350

Gly Pro Gln Leu Gln Ile Leu Glu Glu Met Lys Pro Leu Glu Ser Leu
        355                 360                 365

Ala Leu Glu Glu Ala Ser Gly Pro Val Ser Gln Ser Gln Lys Ser Lys
```

```
                370                 375                 380
Ser Arg Gly Arg Ala Gly Pro Asp Ala Val Thr His Asp Asn Glu Trp
385                 390                 395                 400

Glu Met Leu Ser Pro Gln Pro Val Gln Lys Asn Met Ile Pro Asp Thr
                405                 410                 415

Glu Met Glu Glu Glu Thr Glu Phe Leu Glu Leu Gly Thr Arg Ile Ser
                420                 425                 430

Arg Pro Asn Gly Leu Leu Ser Glu Asp Val Gly Met Asp Ile Pro Phe
                435                 440                 445

Glu Glu Gly Val Leu Ser Pro Ser Ala Ala Asp Met Arg Pro Glu Pro
                450                 455                 460

Pro Asn Ser Leu Asp Leu Asn Asp Thr His Pro Arg Arg Ile Lys Leu
465                 470                 475                 480

Thr Ala Pro Asn Ile Asn Leu Ser Leu Asp Gln Ser Glu Gly Ser Ile
                485                 490                 495

Leu Ser Asp Asp Asn Leu Asp Ser Pro Asp Glu Ile Asp Ile Asn Val
                500                 505                 510

Asp Glu Leu Asp Thr Pro Asp Glu Ala Asp Ser Phe Glu Tyr Thr Gly
                515                 520                 525

His Glu Asp Pro Thr Ala Thr Lys Asp Ser Gly Gln Glu Ser Glu Ser
                530                 535                 540

Ile Pro Glu Tyr Thr Ala Glu Glu Arg Glu Asp Asn Arg Leu Trp
545                 550                 555                 560

Arg Thr Val Val Ile Gly Asp Gln Glu Gln Arg Ile Asp Met Lys Val
                565                 570                 575

Ile Glu Pro Tyr Arg Arg Val Ile Ser His Gly Gly Leu Arg Gly Tyr
                580                 585                 590

Tyr Gly Asp Gly Leu Asn Ala Ile Ile Val Phe Ala Ala Cys Phe Leu
                595                 600                 605

Pro Asp Ser Ser Arg Ala Asp Tyr His Tyr Val Met Glu Asn Leu Phe
                610                 615                 620

Leu Tyr Val Ile Ser Thr Leu Glu Leu Met Val Ala Glu Asp Tyr Met
625                 630                 635                 640

Ile Val Tyr Leu Asn Gly Ala Thr Pro Arg Arg Met Pro Gly Leu
                645                 650                 655

Gly Trp Met Lys Lys Cys Tyr Gln Met Ile Asp Arg Arg Leu Arg Lys
                660                 665                 670

Asn Leu Lys Ser Phe Ile Ile Val His Pro Ser Trp Phe Ile Arg Thr
                675                 680                 685

Ile Leu Ala Val Thr Arg Pro Phe Ile Ser Ser Lys Phe Ser Ser Lys
                690                 695                 700

Ile Lys Tyr Val Asn Ser Leu Ser Glu Leu Ser Gly Leu Ile Pro Met
705                 710                 715                 720

Asp Cys Ile His Ile Pro Glu Ser Ile Ile Lys Tyr
                725                 730
```